United States Patent
Reid et al.

[11] Patent Number: 5,373,571
[45] Date of Patent: Dec. 13, 1994

[54] FIBER OPTIC DIFFUSER TIP

[75] Inventors: Robert A. Reid, Avon; Rudolph A. Montgelas, West Hartford; Robert C. Sullivan, Simsbury; Jon A. Lutzen, Manchester; Michael G. DeCarlo, Waterbury, all of Conn.

[73] Assignee: SpecTran Specialty Optics Company, Avon, Conn.

[21] Appl. No.: 33,193

[22] Filed: Mar. 16, 1993

[51] Int. Cl.⁵ ............................................. G02B 6/34
[52] U.S. Cl. ............................... 385/31; 385/36; 385/43; 385/51; 385/84; 385/128; 385/902
[58] Field of Search ................... 385/31, 36, 51, 43, 385/68, 84, 128, 902

[56] References Cited

U.S. PATENT DOCUMENTS

| | | | |
|---|---|---|---|
| 4,060,308 | 11/1977 | Barnoski et al. | 385/43 |
| 4,413,879 | 11/1983 | Berthold, III et al. | 385/43 |
| 4,445,751 | 5/1984 | Divens et al. | 385/43 |
| 4,660,925 | 4/1987 | McCaughan, Jr. | 385/76 |
| 4,693,556 | 9/1987 | McCaughan, Jr. | 385/147 |
| 4,744,623 | 5/1988 | Prucnal et al. | 385/43 |
| 4,795,228 | 1/1989 | Schneider | 385/31 |
| 4,986,628 | 1/1991 | Lozhenko et al. | 385/31 |
| 4,995,691 | 2/1991 | Purcell, Jr. | 385/29 |
| 5,044,723 | 9/1991 | MacDonald | 385/12 |
| 5,054,867 | 10/1991 | Wagnieres et al. | 385/31 |
| 5,074,632 | 12/1991 | Potter | 385/31 |
| 5,119,461 | 6/1992 | Beyer et al. | 385/147 |

FOREIGN PATENT DOCUMENTS 2154761A  9/1985  United Kingdom .......... G02B 6/00

Primary Examiner—Frank Gonzalez
Attorney, Agent, or Firm—Pennie & Edmonds

[57] ABSTRACT

Photodynamic therapy apparatus providing improved light distribution with an end fitting for use with clad optical fibers, which apparatus cooperates with an unclad stripped terminal end of the optical fiber that is inwardly tapered towards its end such that light scattering media disposed between a glass tube surrounding at least the tapered portion of the optical fiber provides improved and predictable light distribution, the media being suitably cured to a rigid relationship thereby to continuously provide improved light distribution.

6 Claims, 2 Drawing Sheets

FIBER OPTIC DIFFUSER TIP

BACKGROUND OF THE INVENTION

This invention relates to an improved fiber optic diffuser for use in photodynamic therapy (hereinafter PDT). More particularly, the invention is directed to the construction of a fiber optic tip which improves the distribution of light dispersed and propagated from the optical fiber tip to achieve an approximately uniform cylindrical light pattern.

In recent years, PDT has become a common technique in the treatment of cancer through utilization of light-causing chemical reactions. For example, McCaughan, Jr. U.S. Pat. No. 4,660,925 provides a disclosure of many techniques and problems associated with PDT, not the least of which is apparatus that must carry intense radiation without overheating or self-destruction. It has been determined that the apparatus used for PDT laser light transmission along a fiber optic must be able to transmit such intense radiation without developing "hot spots" (optical, thermal or mechanical) and must be able to perform such optical radiating tasks under adverse environmental conditions. It has been known to use a variety of chemical etching techniques and roughening procedures to effect the desired diffusion of light into the desired radiation pattern. In fact, U.S. Pat. No. 4,660,925 makes reference to a Quentron fiber having a tapered point.

OBJECTS OF THE INVENTION

It is a principal object of the present invention to provide improved apparatus for radiating light at the tip of an optical fiber in such a way as to approach the desired uniform cylindrical pattern of light desired for certain types of PDT.

It is a further object of this invention to provide an improved optical fiber tip for PDT which is easy to manufacture and durable in operation while producing the desired light distribution.

It is a further object of this invention to provide the apparatus for a fiber optic tip construction usable in PDT wherein the light distribution pattern is predictable and repeatable by mass manufacturing techniques.

A still further object of the invention is to provide PDT apparatus capable of providing improved light distribution while sustaining the intense optical energy radiation levels without suffering critical optical, thermal or mechanical damage.

Other objects will be in part obvious and in part pointed out more in detail hereinafter.

A better understanding of the invention will be obtained from the following detailed description and accompanying drawings of an illustrative application of the invention.

SUMMARY OF THE INVENTION

The present invention is directed to end fitting apparatus for use with clad optical fibers, which apparatus cooperates with the stripped (unclad) terminal end of an optical fiber, which fiber is inwardly tapered over at least a portion of its length at its end (of reducing diameter toward the distal end) such that light scattering media disposed between a glass tube surrounding at least the tapered terminal fiber portion cooperates with light scattering media disposed between the glass tube of the optical fiber, the media being cured to a rigid relationship. Such an apparatus provides improved light distribution.

DESCRIPTION OF THE PREFERRED EMBODIMENTS

Figure 1:
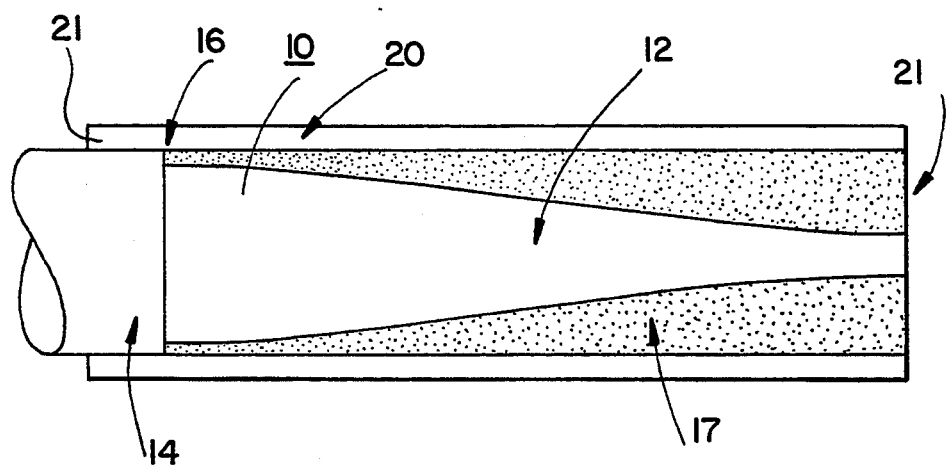

Turning first to FIG. 1, that schematic cross section view shows an optical fiber generally designated 10 which fiber has a tapered end or distal portion generally designated 12, fiber 10 being provided with the conventional hard coating or cladding 14. For purposes to be later described in greater detail, the cladding ends at point 16 leaving a straight portion and tapered end portion of the fiber without cladding.

In accordance with photodynamic therapy (PDT) techniques, light is intended to exit the unclad portion of fiber optic 10 in a controlled manner and in this particular embodiment, monochromatic light from a laser source (not shown) is delivered through fiber optic 10 to activate any suitable photo sensitive drug used in PDT. In many use situations, it is desired to have a fiber optic tip which delivers light in a uniform manner such that, for tumors that have a high aspect ratio (i.e., long and thin) it is desirable to deliver the energy substantially uniformly over the length of the tumor. As pointed out in the prior art, the exposed end portion of the fiber optic is surrounded by a light scattering medium, which light scattering medium generally includes a high refractive index curable epoxy containing 2% to 10% by weight titanium dioxide or aluminum oxide; such prior art establish an RMS particle size of 0.3 to 5 microns with particles forming 5 to 10% of the epoxy mix. It is well known that the amount of light that is dispersed from the optical fiber is generally referred to as scattering power and hence, because of scattering which occurs at the initial end of the unclad portion of the fiber, less light is available at the distal tapered end of the fiber optic; hence to maintain a uniform light intensity, the scattering power must increase if a uniform generally cylindrical pattern is to be attained.

In the present invention, the amount of scattering material increases in a controlled manner as the distal end of tapered fiber optic 10 is approached, which increase is controlled because at lest distal portion 12 of fiber optic 10 is surrounded by a high precision glass capillary 20, which capillary is of constant diameter and the space between the inside wall of glass capillary 20 and fiber portion 12 is filed with the light scattering epoxy mix material. Hence, the amount of light scattering material increases in radial dimension as the end of fiber optic 10 is approached and the light scattering effect along the taper is increased so as to maintain predictability for the emitted light end. However, contrary to many prior art schemes, the amount of scattering material is controlled in the apparatus of this invention by virtue of the nature of the taper of fiber optic end 12 and the spacing of fiber 12 from the inside wall of cylindrical capillary 20. As previously noted, any suitable scattering material and epoxy mix can be used in the present invention, it being desired that the epoxy mix be cured after the fiber optic tip is placed within the glass capillary. If desired, a mirror end face 21 can be provided.

The desirable centering of fiber 12 in capillary tube 20 is assisted by extending portion 21 of glass capillary 20 over the clad portion and in close engagement with clad portion 14 of the fiber thereby to establish a self-centering relationship for that end of the capillary 20 relative to fiber optic 10.

An important advantage of the present invention is that small (approximately 5.5 micron size) alumina particles can be placed in light scattering mix 17 thereby to ensure a wall separation between the inside diameter of the capillary 20 wall and fiber optic portion 12 of at least 5.5 microns thereby to act as an additional centering technique which ensures that the fiber will not come in contact with the capillary wall thereby to avoid unwanted reflections or hot spots or other energy non-uniformity in the light distribution pattern. Hence, with one end of capillary 20 engaging and centered by cladding 14 and upon curing, tapered end 12 of fiber optic 10 is fixedly positioned within capillary tube 20, thereby to provide repeatable and predictable light distribution patterns.

The positioning of fiber optic 10 and particularly fiber optic end portion 12 within capillary tube 20 is even more closely controlled (prior to epoxy curing) by adding glass or ceramic particles in the size range of 5 of 10 microns to the scattering mix to improve the centering, spacing action between the capillary 20 and fiber optic portions 10 and 12. More specifically, such glass or ceramic material having an index of refraction close to that of the selected epoxy further ensures separation of the fiber tip 12 from the capillary wall 20. Such a spacing technique tends to eliminate multiple beam interference effects caused by small separations and to increase the predictability and uniformity of light distribution.

Figure 2:
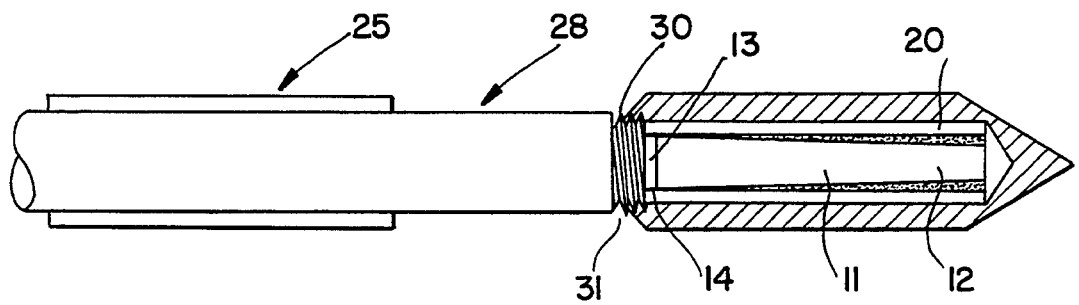

Turning next to FIG. 2, a more commercial appearing apparatus is disclosed in cross section form showing cable jacket 25 which has been removed to expose the buffer coating 28, usually a TEFZEL ® (registered trademark of duPont), which buffer is provided with embossed threads 30 at its end 31. Clad portion 14 and unclad portion 11 of the fiber optic 10, with the fiber optic tapered end 12 being provided with a tapered portion and a substantially straight portion 13 over which the capillary tube 20 extends; the housing 30 is preferably a polycarbonate material which is, for the most part, transparent to the laser light wavelength being used, the housing being provided with internal threads 31 that cooperate with the threads provided on the buffer 30. Pointed end 32 may have any desired configuration as determined by the use environment.

It should be observed that the straight portion of the fiber exists within the capillary and is untapered until it begins to reach the prescribed diameter of the distal end of the diffuser. The use of that straight section within the capillary tube permits control of the initial light distribution. That same straight portion is used for positioning of the fiber optic tip relative to the capillary tube. Similarly, by controlling the amount of light released over the straight portion of the fiber, the distribution of light over the entire length of the taper is subjected to better control.

Figure 3:
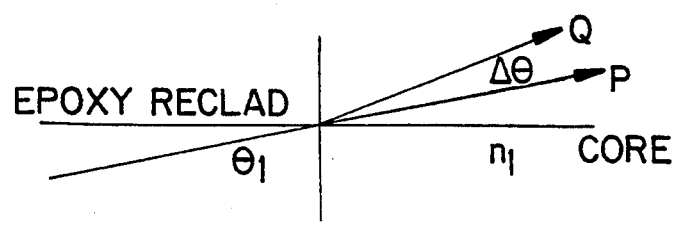

Turning next to FIG. 3, use of an optical adhesive material (epoxy) with a fiber core requires understanding of the refractive index of each. In FIG. 3, arrow P indicates the expected path of a light ray incident on a core/epoxy interface such that the angle of retraction equals the angle of incidence. In the case of the epoxy fiber relationship of the present invention, the index of refraction of the epoxy and the fiber is not mated; the epoxy index is preferably selected to be 1.52. The ray preceding along the direction Q will depart from the normal straight trajectory P by an amount generally determined by Snell's Law.

$\Delta\theta$ represents the angular change in refracted ray angle caused by a given change, $\Delta n$, in the reclad epoxy refractive index (relative to core index); hence, a real change in path direction occurs as the epoxy index of refraction departs from the core index of refraction because, in the present invention, $\Delta\theta$ is $\neq 0$, and this emphasizes a feature of the invention whereby the epoxy refractive index does not match the refractive index of the fiber core.

Figure 4:
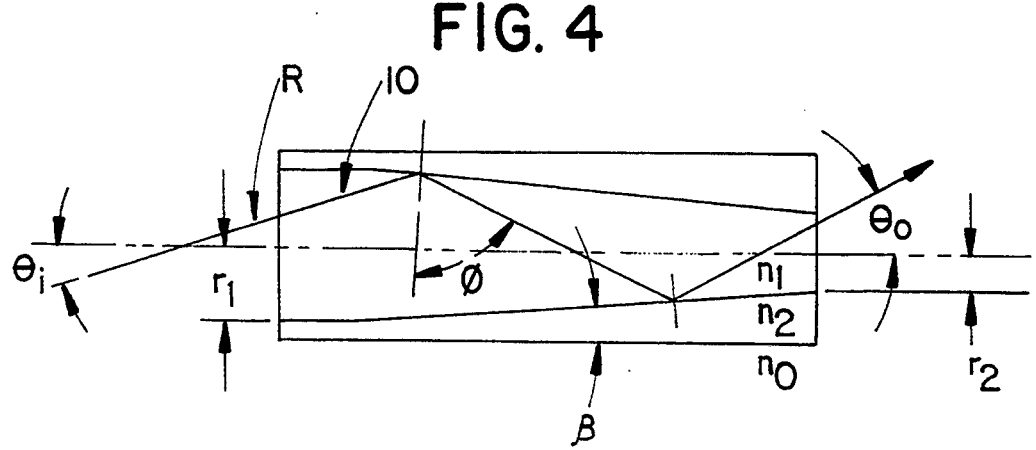

Turning next to FIG. 4, there is shown a schematic diagram of the path of typical light ray action in the fiber optic tip of the present invention. The meridonal ray R incident upon the large end of the taper of the fiber 10 at the angle $\theta i$ (formed with the axis of the fiber) is reflected from the conical wall at progressively lower angles of incidence. Starting at an initial value of $\theta i$, the propagation angle $\theta$ will increase by $2\beta$ at each reflection at the core clad interface. If the fiber taper is smooth and the number of reflections is great, $\theta o$ is given value by the relationship:

$$\sin \theta o = \frac{r1}{r2} \cdot \sin \theta i$$

When $\phi$ becomes less than the critical angle so that the ray is no longer guided by the core, it will pass to the cladding and impinge upon the scattering media. Hence, the ray will escape into the region of index $n_o$ when:

$$\sin \theta o \geq \sin \theta_{Omax} = \frac{(n_1^2 - n_o^2)^{\frac{1}{2}}}{n_1} = \frac{NA}{n_1}$$

This equation is of course for the case of absence of scattering media. With scattering media present, the efficiency of coupling of rays to the region of the index $n_o$ will vastly increase.

All of the foregoing is intended to establish a theory of operation for the unique structure which creates an opportunity for more specific repetitive predictable control over the light distribution intensity in a PDT light probe.

The methods of securing fiber taper, mixing the scattering compound, etc. do not form a part of this invention with the exception that the provision of particles of a certain preselected particle for the scattering medium and a particle size of the glass or ceramic particles is selected to ensure proper centering of the tapered end of the fiber within the capillary tube. The mounting of the capillary tube on the clad fiber to assist in producing concentricity of that end of the capillary relative to the tapered fiber, the curing of the epoxy, are all believed to be matters of importance in the pragmatic utilization of the invention.

Although the invention has been illustrated and described with respect to exemplary embodiments thereof, it should be understood by those skilled in the art that the foregoing and various other changes, omissions and additions may be made therein and thereto without departing from the spirit and scope of the invention.

We claim:

1. Photo dynamic therapy apparatus comprising:
   a clad optical fiber having a straight clad portion and an end portion from which the cladding has been removed to provide clad and unclad end portions;

said end portions having a straight, generally cylindrical fiber portion and a terminal portion having an inwardly tapered longitudinal cross section;

a glass tube surrounding the straight clad optional fiber end portion including at least the unclad tapered terminal portion, said tube having a substantially constant internal diameter greater than the outside diameter of unclad fiber portion; and light scattering media disposed between and filling the space between said glass tube and at least the unclad portion of said optical fiber whereby light is diffused in a controlled manner from the inwardly tapered terminal portion, the space between the inside wall of said glass tube and the optical fiber end portion being substantially filled with a material curable to rigidly position said tube relative to said unclad fiber end portion after curing.

2. Apparatus of claim 1 wherein said curable material is an epoxy including light scattering particles, some of which have a size tending to center the fiber end portion within said tube.

3. The apparatus of claim 2 wherein the end of the optical fiber end portion is coterminous with said glass tube.

4. The apparatus of claim 2 wherein the light scattering particles include glass beads which are substantially transparent to the laser frequency light and assist in positioning the fiber end coaxial with tube.

5. Apparatus for use in photo dynamic therapy for irradiating human body portions comprising:

a clad optical fiber having an end portion from which the cladding is removed;

a glass tube surrounding the clad and unclad portions of the optical fiber, said tube being coextensive with the unclad portion and at least a portion of the clad portion, said tube being of an inside diameter to be closely spaced from the clad portion of the fiber;

the unclad portion of the fiber being tapered from the region of the clad portion to the distal fiber end, and a curable epoxy filling the space between the fiber and the tube to rigidly position the tube relative to the fiber end portion.

6. The apparatus of claim 5 wherein the epoxy contains light scattering particles.

* * * * *